US006893634B1

(12) United States Patent
Günzburg et al.

(10) Patent No.: US 6,893,634 B1
(45) Date of Patent: May 17, 2005

(54) ENCAPSULATED CELLS PRODUCING CYTOCHROME P450

(75) Inventors: Walter H. Günzburg, Mölding (AT); Peter Karle, Vienna (AT); Robert Saller, München (DE); Brian Salmons, Markt Indersdorf (DE); Matthias Löhr, Rostock (DE); Peter Müller, Rostock (DE)

(73) Assignees: GSF-Forschungszentrum fur Umwelt und Gesundheit GmbH, Neuherberg (DE); Bavarian Nordic A/S, Kvistgard (DK)

(*) Notice: Subject to any disclaimer, the term of this patent is extended or adjusted under 35 U.S.C. 154(b) by 0 days.

(21) Appl. No.: 09/160,067

(22) Filed: Sep. 24, 1998

Related U.S. Application Data

(63) Continuation-in-part of application No. PCT/EP97/01585, filed on Mar. 27, 1997.

(30) Foreign Application Priority Data

Mar. 27, 1996 (DK) .............................. 0352/96

(51) Int. Cl.[7] ........................ A01N 63/00; A01N 43/04; A61K 49/00; C12N 5/00; C12N 15/63
(52) U.S. Cl. ...................... 424/93.21; 424/91; 424/9.2; 424/93.1; 424/93.2; 435/69.1; 435/320.1; 435/325; 435/382; 435/455; 514/2; 514/44
(58) Field of Search .............................. 435/69.1, 320.1, 435/325, 455, 382, 183, 189, 6; 424/93.1, 93.2, 93.21, 9.1, 9.2, 451; 514/2, 44; 536/23.2

(56) References Cited

FOREIGN PATENT DOCUMENTS

| WO | WO 89/11539 | 11/1989 |
|----|-------------|---------|
| WO | WO 94/29437 | 12/1994 |
| WO | WO 96/04789 | 2/1996 |
| WO | WO 96/07748 | 3/1996 |
| WO | WO 97/01357 | 1/1997 |
| WO | WO 97/09440 | 3/1997 |
| WO | WO 97/35994 | 11/1997 |

OTHER PUBLICATIONS

U.S. Appl. No. 08/996,460, filed on Dec. 23, 1997, entitled "Encapsulated Cells Producing Viral Particles", by Robert Michael Saller, Walter H. Günzburg and Brian Salmons.
Wright, J.E., et al., "Analysis of 4–Hydroxycyclophosphamide in Human Blood", *Analy. Biochem.*, 224(1) : 154–158 (1995).
Connors, T.A., "The choice of prodrugs for gene directed enzyme prodrug therapy of cancer", *Gene Ther.*, (10) : 702–709 (1995).
Salmons, B., et al., "Construction of Retroviral Vectors for Targeted Delivery and Expression of Therapeutic Genes", *Leukemia*, 9(Supplement 1) :S53–S60 (1995).

Wei, M.X., et al., "Experimental Tumor Therapy in Mice Using the Cyclophosphamide–Activating Cytochrome P450 2B1 Gene", *Human Gene Ther.*, 5(8):969–978 (1994).
Chen, S.–H., et al., "Gene therapy for brain tumors: Regression of experimental gliomas by adenovirus–mediated gene transfer in vivo", *Proc. Natl. Acad. Sci. USA*, 91(8):3054–3057 (1994).
Donato, M.T., et al., "A Microassay for Measuring Cytochrome P450IA1 and P450IIB1 Activities in Intact Human and Rat Hepatocytes Cultured on 96–Well Plates", *Analyt. Biochem.*, 213(1):29–33 (1993).
Freeman, S.M., et al., "The "Bystander Effect": Tumor Regression When a Fraction of the Tumor Mass is Genetically Modified", *Can. Res.*, 53(21):5274–5283 (1993).
Vile, R. G. and Hart, I. R., "Use of Tissue–specific Expression of the Herpes Simplex Virus Thymidine Kinase Gene to Inhibit Growth of Established Murine Melanomas following Direct Intratumoral Injection of DNA", *Can. Res.*, 53(17):3860–3864 (1993).
Bi, W. L., et al., "In Vitro Evidence That Metabolic Cooperation Is Responsible for the Bystander Effect Observed with HSV tk Retroviral Gene Therapy", *Human Gene Ther.*, 4(6):725–731 (1993).
Ram, Z., "In Situ Retroviral–mediated Gene Transfer for the Treatment of Brain Tumors in Rats", *Can. Res.*, 53(1):83–88 (1993).
Tiano, H. F., et al., "Retroviral mediated expression of human cytochrom P450 2A6 in C3H/10T1/2 cells confers transformability by 4–(methylnitrosamino)–1–(3–pyridyl)–1–butanone (NNK)", *Carcinog.*, 14(7):1421–1427 (1993).
Salmons, B. and Günzburg, w. H., "Targeting of Retroviral Vectors For Gene Therapy", *Human Gene Ther.*, 4(2):129–141 (1993).
Culver, K. W., "In Vivo Gene Transfer with Retroviral Vector–Producer Cells for Treatment of Experimental Brain Tumors", *Sci.*, 256:1550–1552 (1992).
Kedzie, K. M., et al., "Molecular Basis for a Functionally Unique Cytochrome P450IIB1 Variant", *J. Biol. Chem.*, 266(33):22515–22521 (1991).

(Continued)

*Primary Examiner*—Jeffrey Fredman
*Assistant Examiner*—Sumesh Kaushal
(74) *Attorney, Agent, or Firm*—Hamilton, Brook, Smith & Reynolds, P.C.

(57) ABSTRACT

The present invention relates to capsules encapsulating cytochrome P450 producing cells and cytochrome P450 producing retroviral packaging cells. Furthermore, the present invention relates to the treatment of cancer or any other relevant disease with said capsules and to the use of said capsules for the preparation of a pharmaceutical composition for said treatment.

21 Claims, No Drawings

OTHER PUBLICATIONS

Kolb, A.F., "Characterization of a Protein that Binds a negative Regulatory Element in the Mammary-Specific Whey Acidic Protein Promoter", *Biochem. Biophys. Res. Comm., 217*(3):1045–1052 (1995).

Salmons, B., et al., "Production of Mouse Mammary Tumor Virus upon Transfection of a Recombinant Proviral DNA into Cultured Cells", *Virol., 144*:101–114 (1985).

Fujii–Kuriyama, Y., et al., "Primary structure of a cytochrome P–450 Coding nucleotide sequence of phenobarbital–inducible cytochrome P–459 cDNA from rat liver", *Proc. Natl. Acad. Sci. USA, 79*:2793–2797 (1982).

Connors, T. A., "Prodrugs in cancer chemotherapy", Xenobiot., 16(10/11):975–988 (1986).

Connors, T. A. and Whisson, M. E., "Cure of Mice bearing Advanced Plasma Cell Tumours with Aniline Mustard: the Relationship between Glucuronidase Activity and Tumour Sensitivity", *Nature, 210*:866–867 (1966).

SEQUENCE LISTING

```
<160> NUMBER OF SEQ ID NOS: 6

<210> SEQ ID NO 1
<211> LENGTH: 26
<212> TYPE: DNA
<213> ORGANISM: Artificial Sequence
<220> FEATURE:
<223> OTHER INFORMATION: Left Hand PCR Primer used for  preparation of
      CYP2BI gene

<400> SEQUENCE: 1
cgtgcggaat tcggcggatt cagcat                                          26

<210> SEQ ID NO 2
<211> LENGTH: 26
<212> TYPE: DNA
<213> ORGANISM: Artificial Sequence
<220> FEATURE:
<223> OTHER INFORMATION: Right Hand PCR Primer used for preparation of
      CYP2BI gene

<400> SEQUENCE: 2
ataacggata tcacctggct gcctca                                          26

<210> SEQ ID NO 3
<211> LENGTH: 26
<212> TYPE: DNA
<213> ORGANISM: Artificial Sequence
<220> FEATURE:
<223> OTHER INFORMATION: Left Hand PCR Primer with a SspBI restriction
      site for preparation of a retroviral expression vector containing
      rat cytochrome P450 2BI

<400> SEQUENCE: 3
aagcctgtac actggagagc atgcac                                          26

<210> SEQ ID NO 4
<211> LENGTH: 26
<212> TYPE: DNA
<213> ORGANISM: Artificial Sequence
<220> FEATURE:
<223> OTHER INFORMATION: Right Hand PCR Primer with a SspBI restriction
      site for preparation of a retroviral expression vector containing
      rat cytochrome P450 2BI
```

```
-continued

<400> SEQUENCE: 4
cgattactcg agacctggct gcctca                                            26

<210> SEQ ID NO 5
<211> LENGTH: 26
<212> TYPE: DNA
<213> ORGANISM: Artificial Sequence
<220> FEATURE:
<223> OTHER INFORMATION: PCR Primer with a BamHI site for preparation of
      a retroviral vector containing WAP

<400> SEQUENCE: 5
aagccggatc cctggagagc atgcac                                            26

<210> SEQ ID NO 6
<211> LENGTH: 20
<212> TYPE: DNA
<213> ORGANISM: Artificial Sequence
<220> FEATURE:
<223> OTHER INFORMATION: PCR Primer with a BamHI site for preparation of
      a retroviral vector containing WAP

<400> SEQUENCE: 6
cgattaggat ccctgcctca                                                   20
```

ENCAPSULATED CELLS PRODUCING CYTOCHROME P450

RELATED APPLICATION(S)

This is a Continuation-in-Part application of PCT/EP97/01585 filed Mar. 27, 1997 which claims priority to Danish patent application DK 0352/96 filed Mar. 27, 1996. The contents of PCT/EP97/01585 and DK 0352/96 are incorporated herein by reference in their entirety.

BACKGROUND OF THE INVENTION

The anti-cancer drugs used to treat tumours are in most cases applied systemically and spread through the whole body of the patient. The high systemic dose of such drugs required for cancer treatment is combined with unpleasant side-effects for the patient.

In an attempt to circumvent this problem, cancer-prodrugs that have to be metabolized or activated in the body before they become cytotoxic have been used. Unfortunately, human tumours that contain appropriate high levels of the activating enzymes are rare. The main site for activation of prodrugs is the liver and to ensure that a tumour, at a distant site, receives a sufficient dose of the activated drug, the amount of activated prodrug produced in the liver has to be quite high and again this leads to toxic side effects for the patient.

One strategy by which these problems of high systemic concentration of activated drugs could be circumvented would be to provide means for activation of the prodrug directly in or near the site of the tumour. This strategy would require that tumour cells, or cells at the site of a tumour are genetically transformed to produce high amounts of the enzymes required for metabolizing the cancer prodrugs. Retroviral vectors are ideally suited for the stable delivery of genes to cells since the retrovirus is able to integrate the DNA form of its genome into the genome of the host cell and thus all daughter cells of an infected cell will carry the retroviral vector carrying the therapeutic gene. A further advantage is that most retroviruses only infect dividing cells and they are therefore ideal gene delivery vehicles for tumour cells.

Retroviral vectors are the most commonly used gene transfer vehicles for the clinical trials that have been undertaken to date. Most of these trials have, however, taken an ex vivo approach where the patient's cells have been isolated, modified in culture and then reintroduced into the patient.

The delivery of genes in vivo introduces a variety of new problems. First of all, and above all, safety considerations have to be addressed.

A major concern for eventual in vivo gene therapy, both from a safety stand point and from a purely practical stand point, is the targeting of the expression. It is clear that therapeutic genes carried by vectors should not be indiscriminately expressed in all tissues and cells, but rather only in the requisite target cell. This is especially important when the genes to be transferred are such prodrug activating genes designed to ablate specific tumour cells. Ablation of other, non-target cells would obviously be very undesirable.

The essentially random integration of the proviral form of the retroviral genome into the genome of infected cells has posed a serious ethical problem because such random integration may lead to activation of proto-oncogenes and thus lead to the development of a new cancer. Most researchers would agree that the probability of a replication defective retrovirus, such as all those currently used, integrating into or near a cellular gene involving in controlling cell proliferation is vanishingly small. However, it is generally also assumed that the explosive expansion of a population of replication competent retroviruses from a single infection event, will eventually provide enough integration events to make such a phenotypic integration a very real possibility.

Retroviral vector systems are optimized to minimize the chance of replication competent virus being present. It has however, been well documented that recombination events between components of the retroviral vector system can lead to the generation of potentially pathogenic replication competent virus and a number of generations of vector systems have been constructed to minimize this risk of recombination (Salmons, B. and Günzburg, W. H., *Human Gene Therapy*, 4(2):129–41 (1993).

Retroviral vector systems consist of two components:

1) The retroviral vector itself is a modified retrovirus (vector plasmid) in which the genes encoding for the viral proteins have been replaced by therapeutic genes. Since the replacement of the genes encoding for the viral proteins effectively cripples the virus it must be rescued by the second component in the system which provides the missing viral proteins to the modified retrovirus.

The second component is:

2) A cell line that produces large quantities of the viral proteins, however lacks the ability to produce replication competent virus. This cell line is known as the packaging cell line and consists of a cell line transfected with one or more plasmids carrying the genes enabling the modified retroviral vector to be packaged.

To generate a recombinant retroviral particle, the retroviral vector is transfected into the packaging cell line. Under these conditions the modified retroviral genome including the inserted therapeutic gene is transcribed from the retroviral vector and packaged into the modified retroviral particles. These recombinant retroviral particles are then used to infect tumour cells during which the vector genome and any cytotoxic gene becomes integrated into the target cell's DNA. A cell infected with such a recombinant viral particle cannot produce new vector virus since no viral proteins are present in these cells but the DNA of the vector carrying the therapeutic is integrated in the cell's DNA and can now be expressed in the infected cell.

A number of retroviral vector systems have been previously described that should allow targeting of the carried cytotoxic genes (Salmons, B. and Gunzburg, W. H. *Human Gene Therapy*, 4(2):12941 (1993)). Most of these approaches involve either limiting the infection event to predefined cell types or using heterologous promoters to direct expression of linked heterologous therapeutic genes to specific tumour cell types. Heterologous promoters are used which should drive expression of linked genes only in the cell type in which this promoter is normally active or/and additionally controllable. These promoters have previously been inserted, in combination with the therapeutic gene, in the body of the retroviral vectors, in place of the gag, pol or env genes.

The retroviral Long Terminal Repeat (LTR) flanking these genes carries the retroviral promoter, which is generally non-specific in that it can drive expression in many different cell types (Majors, J. (1990), in "Retroviruses—Strategies of replication (Swanstrom, R. and Vogt, P. K., Eds.): Springer-Verlag, Berlin: 49–92). Promoter interference between the LTR promoter, and heterologous internal promoters, such as the tissue specific promoters, described above, has been reported. Additionally, it is known that retroviral LTR's harbour strong enhancers that can, either independently, or in conjunction with the retroviral promoter, influence expression of cellular genes near the site of integration of the retrovirus. This mechanism has been shown to contribute to tumourigenicity in animals (van Lohuizen, M. and Berns, A. (1990), *Biochim. Biophys. Acta,* 1032:213–235). These two observations have encouraged the development of Self-Inactivating-Vectors (SIN) in which retroviral promoters are functionally inactivated in the target cell (WO 94/29437). Further modifications of these vectors include the insertion of promoter gene cassettes within the LTR region to create double copy vectors (WO 89/11539). However, in both these vectors the heterologous promoters inserted either in the body of the vector, or in the LTR region are directly linked to the therapeutic gene.

The previously described SIN vector mentioned above carrying a deleted 3'LTR (WO 94/29437) utilizes in addition a heterologous promoter such as that of Cytomegalovirus (CMV), instead of the retroviral 5'LTR promoter (U3-free 5'LTR) to drive expression of the vector construct in the packaging cell line. A heterologous polyadenylation signal is also included in the 3'LTR (WO 94/29437).

A variety of cytotoxic genes carried by retroviral vectors have already been tested. These genes encode enzymes which convert substances that are pharmacodynamically and toxicologically inert even at high dose-levels but which can be converted in vivo to highly active metabolites (Connors, T. A., *Gene Therapy,* 2:702–709 (1995)).

In cancer chemotherapy appropriately designed prodrugs have been found to be effective in the treatment of animal tumours possessing high levels of an activating enzyme (Connors, T. and Whisson, M., *Nature,* 210:866 867 (1966); Cobb, L. et al., *Biochemical Pharmacology,* 18:1519–1527 (1969)). Clinical results were, however, disappointing since it was found that human cancers that contained appropriately high levels of activating enzymes were rare (Connors, T., *Xenobiotica,* 16:975–988 (1986)). Viral directed enzyme prodrug therapy (VDEPT) and the more general gene directed enzyme prodrug therapy (GDEPT) are related in that they also aim to destroy tumour cells by the tumour specific activation of a prodrug. However, in this case, the gene encoding the enzyme is either specifically targeted to malignant cells or is under the control of a specific promoter.

Up to now most of the efforts directed towards prodrug therapy have concentrated on the use of the human Herpes Simplex Virus thymidine kinase (HSV-tk) as a suicide gene. Although the HSV-tk enzyme in combination with the prodrug ganciclovir (GCV) has been recommended as a good system for GDEPT (Culver, K. et al., *Science,* 256:1550–1552 (1992); Ram, Z. et al., *Cancer Research* 53:83–88 (1993); Chen, S. Shine, H. et al., *Proc. Natl. Acad. Sci.,* 91:3054–3057 (1994)) there are a number of theoretical considerations that would suggest that it is by no means the best combination. First, it is an S-phase specific agent with no effect on resting cells. This is because the GCV monophosphate is short lived and has to be present when cells are entering the S-phase to give a toxic effect. The HSV-tk phosphorylates GCV to the monophosphate form (a reaction that cannot be performed by mammalian enzymes) which is then phosphorylated by cellular enzymes to the triphosphate form and incorporated into DNA. Second, the active drug is a triphosphate and would not be expected to diffuse freely to cause a bystander effect. However a bystander effect has been observed both in vitro and in vivo although metabolic cooperation appears to be involved and in the latter case some of the effect may be an indirect one involving an immune component (Bi, W., Parysek, L. et al., *Human Gene Therapy,* 4:725–731 (1993); Vile, R. and Hart, I., *Cancer Research,* 53:3860–3864 (1993) and Freeman, S., Abboud, C. et al., *Cancer Research,* 53:5274–5283 (1993)). One disadvantage is that the bystander effect is dependent on a cell—cell contact. This may be due to the presence of gap junctions formed by intimate contact between the transduced and the surrounding cells which enable the transfer of phosphorylated ganciclovir.

Recently, interesting results have been reported with cells that have been transfected with the gene encoding the rat cytochrome P450 form 2B1 and then treated with cyclophosphamide (Chen, S., Shine, H et al., *Proc. Natl. Acad. Sci.,* 91:3054–3057 (1994)).

Cytochrome P450's form a broad group of monooxygenases that catalyze oxidation of a wide range of substrates. They are produced by some bacteria, yeast, and by higher organisms, where they play a role in detoxification of xenobiotics, bioactivation reactions, and metabolism of various endogenous compounds.

Cytochrome P450 catalyzes the hydroxylation of the commonly used cancer prodrugs cyclophosphamide (CPA) and ifosfamide to their active toxic forms. Normally the expression of the patient's endogenous cytochrome P450 gene is limited to the liver, and anti-tumour effects of systemically applied CPA depends upon the subsequent systemic distribution of toxic drug metabolites from the liver. This has led to toxicity problems since the activated drug not only affects the tumour but also affects other normal patient tissues such as bone marrow and kidney.

A therapeutic approach to overcome said systemic toxicity problems would be a direct delivery of the activated metabolites. Unfortunately said metabolites have after in vitro production a short half life of about 30 min. (Sladek, N. E., Powers, J. F. & Grage, G. M., Half-life of oxazaphosphorines in biological fluids. *Drug Metab. Dispos.,* 12, 553–559 (1984)).

Thus, in an alternative therapeutic approach, as addressed in PCT/US95/10365, the cytochrome P450 gene is selectively introduced directly into tumour cells, and overexpressed in these cells. Toxic metabolites produced from the transduced cells affect surrounding non-transduced tumour cells in a concentration gradient dependent manner. An additional advantage of the cytochrome P-450/CPA system is the lack of dependency upon cell replication for cytotoxic effects on the surrounding cells. This is because one of the active metabolites generated causes interstrand crosslinks regardless of the cell cycle phase. Later on, during DNA synthesis, these interstrand crosslinks result in cell death.

For the treatment of cancers, it would be feasible to isolate cells from a patient (either tumour cells or normal cells) infect them in vitro with a recombinant retroviral particle carrying a gene encoding cytochrome P450, and then return them to the patient in the vicinity of the tumour. However, this approach is extremely labor intensive because each patient cells must be isolated, cultured, transduced with the gene construct and successfully returned without infection by adventitious agents. The cost and time involved in such an approach limits its practical usefulness. Moreover, most tumours are not suitable for ex vivo gene therapy.

Ideally, the gene encoding cytochrome P450 should be introduced in vivo into the tumour cells, or into cells in the vicinity of the tumour. PCT/US95/10365 suggests an in vivo infection of such cells with isolated retroviral particles. Unfortunately, retroviral particles have a very short half life in vivo and additionally, said particles are very quickly cleared by the immune system. Thus, the infection efficiency in normal tumours and thereby the expression of the prodrug activating enzyme in tumour cells is very poor.

In a further set-up of PCT/US95/10365 cytochrome P450 producing retroviral packaging cells were injected into the brain to provide the retroviral particles and additionally the activating enzyme at the site of a tumour. Even if, using this approach, the amount of activating enzyme could be increased, compared to the efficiency of only an infection with retroviral particles, it nevertheless has the drawback that this approach is clearly limited to the brain, since only the less active immune system in the brain would tolerate the injection of packaging cells, which is derived from a different organism.

Thus, it would be highly desirable if an approach could be envisaged, where one type of cells is transfected with the gene encoding P450 or infected with a recombinant retroviral particle carrying a gene encoding P450, and then used for therapy of many different patients as well as for many different tumours. Such an approach is much more feasible, assuming that problems of immune rejection can be overcome without weakening the patients immune status.

SUMMARY OF THE INVENTION

It is thus an object of the present invention to provide means, which allow the release of cytochrome P450 for the treatment of cancer or any other relevant disease without incidence of inflammatory or any other immune responses.

The invention inter ala comprises the following, alone or in combination:

A capsule encapsulating a cytochrome P450 producing cell, said capsule comprising a porous membrane which is permeable to cytochrome P450 produced by said cell;

the capsule as above, wherein the capsule material comprises a complex formed from cellulose sulphate and polydimethyldiallylammonium;

the capsule as any above, wherein the cytochrome P450 producing cell is a packaging cell line comprising a retroviral vector carrying the cytochrome P450 gene, said packaging cell line habouring at least one retroviral or recombinant retroviral construct coding for the proteins required for said retroviral vector to be packaged;

the capsule as above, wherein the retroviral vector is replication-defective;

the capsule as any above, wherein the retroviral vector comprises a 5' LTR region of the structure U3-R-U5; one or more sequences selected from coding and non-coding sequences wherein at least one of the coding sequences codes for cytochrome P450; and a 3'LTR region comprising a completely or partially deleted U3 region wherein said deleted U3 region is replaced by a polylinker sequence, followed by the R and U5 region;

the capsule as any above, wherein the cytochrome P450 gene is under transcriptional control of a target cell specific regulatory element or promoter, and/or an X-ray inducible promoter;

the capsule as any above, wherein the retroviral vector is a vector prepared as described in Example 2;

the capsule as above, wherein said cytochrome P450 producing cell comprises a vector prepared as described in Example 1;

the capsules as any above, wherein the encapsulated cells produce 0.1 to 10 pmol cytochrome P450 per $10^5$ cells;

a pharmaceutical composition comprising the capsule as any above;

the capsule as any above for use in the treatment of cancer or any other relevant disease or disorder;

use of the capsule as any above for producing a pharmaceutical composition useful for the ablation of tumour cells;

a method of treating cancer or any other relevant disease or disorder comprising administering to a subject in need thereof a therapeutically effective amount of the capsule as any above and, either simultaneously or with a time span, a prodrug which is activated by cytochrome P450;

the method as above, wherein the prodrug is provided as a slow release preparation;

the method as any above, wherein the prodrug is encapsulated into a capsule comprising a porous membrane;

the method as any above, wherein the capsule is administered by injection and/or by implantion into the target organ and/or close to the site of said target organ, and the prodrug is administered systemically and/or locally;

the method as any above, wherein the capsule is administered by intra-arterial injection;

the method as any above, wherein the target organ comprises cells of breast tumours and/or pancreatic tumours;

the method as any above, wherein the prodrug is cyclophosphamide and/or ifosfamide;

the method as any above, wherein 10 to 100 mg per $m^2$ body surface of said prodrug are administered to a subject in need thereof.

DETAILED DESCRIPTION OF THE INVENTION

To achieve the foregoing and other objects, the present invention provides a capsule encapsulating cytochrome P450 producing cells, said capsule comprising a porous membrane which is permeable to cytochrome P450 produced by said cells. This capsule can be administered to a patient to increase at a desired location the amount of the liver enzyme cytochrome P450. Thus, the encapsulated cells injected or implanted into an individual provide a small prodrug conversion factory that can be near or in the tumour mass. According to one embodiment of the present invention the encapsulated cells produce about 0.1 to about 10 pmol cytochrome P450 per $10^5$ cells. The cytochrome P450 released from said capsules in combination with a systemic or local application of ifosfamide or cyclophosphamide leads to high local concentrations of the activated metabolites, since cytochrome P450 hydroxylates said commonly used cancer prodrug to their toxic metabolites. This high local concentrations of said toxic metabolites affects surrounding tumour cells in a concentration gradient dependent manner without further systemic toxicity for the patient. Thus, the present invention provides novel means for an effective and well tolerable treatment of cancer or any other proliferative disease or disorder.

In one embodiment of the present invention the capsules encapsulate retroviral packaging cells which comprise a retroviral vector carrying the cytochrome P450 gene. Additionally, said packaging cells incorporates DNA which encodes for all proteins required for a retroviral particle to be packaged. Accordingly, said packaging cells produce the cytochrome P450 and additionally release retroviral particles, which themselves can transduce further cells by infection and subsequent integration of their vector genome carrying the cytochrome P450 gene into the genome of the infected cells. Thus, the encapsulated packaging cells producing said retroviral particles constitute a small virus producing factory, which can be placed at the site of application. This will allow efficient long term delivery of the recombinant virus in vivo.

The long term effectivity of this approach depends on (1) protection of the cells from the host immune system, which would normally eliminate virus producing or infected cells, especially if the cells are from a different species as is usually the case for retroviral vector producing cells and (2) survival of the cells in situ for extended periods, which may require vascularisation.

It has been found that the continuous production of a vector virus from implanted packaging cells can be achieved by the appropriate encapsulation, in microcapsules with semipermeable membranes, of the virus producing packaging cells before implantation. Additionally, it has been found that such capsules become well engrafted in the host, become vascularized, and do not elicit a host immune or inflammatory response. These findings, together with the semipermeability of the capsule membrane, permits long term retroviral vector delivery in vivo.

The pores in the porous membrane of the capsules according to the present invention have a size that allows cytochrome P450, any nutrition factors or viral particles to penetrate, but is not permeable for any cell of the immune system. Thus, cytochrome P450 producing cells inside the capsules are completely protected from cells of the host immune system and thus, induce no immune reaction even if said cells are allogenic or xenogenic.

The term "allogenic" describes genetic differences within species, that is e.g. differences in cell surface markers such as MHC molecules on lymphocytes from genetically non-identical individuals. Allogenic cells are therefore simply those from another individual of the same species. In contrast thereto, the term "xenogenic" describes genetic differences between different species. Consequently, xenogenic cells are those from every other individual except representatives of the same species.

Due to said immune protection by the capsules the present invention therefore provides the possibility to encapsulate any allogenic or xenogenic cells that are transfected with an expression vector encoding the cytochrome P450 gene. In the typical expression vector according to the present invention the cytochrome P450 gene is under the transcriptional control of a strong constitutive promoter, such as the CMV promoter. Alternatively, an inducible or a X-ray dependent promoter can be used for expression of the cytochrome P450 gene. Said expression vectors are transfected into cells, according to standard protocols and subsequently, populations or clones of transduced cells, which produce about 0.1 pmol to about 10 pmol of cytochrome P450 are selected, characterized and encapsulated.

An encapsulation technology providing for the encapsulation of virus producing packaging cells, and of virus infected or normal cells in a non immunogenic, specifically in a cellulose based material, has been developed. Using this technique up to $10^{10}$, but preferably $10^5$–$10^7$ cells are encapsulated in electrolyte complex (e.g. from alginate and polylysine or, more preferably, cellulose sulphate and polydimethyldiallylammonium chloride) or other porous structures (such as polyamides, polysulfones). The resulting capsules have a variable diameter between 0.01 and 5 mm, but preferably 0.1 and 1 mm. Consequently, capsules can be made to contain a variable number of cells. The capsule is semipermeable with pores that are large enough to allow viruses or prodrug molecules to pass through but small enough to prevent cells of the immune system from accessing the cells thereby significantly reducing an immune response to these cells. The capsules and the encapsulated cells are cultivated in a normal cell culture medium (the nature of which depends on the cell line encapsulated) at standard conditions of humidity, temperature and $CO_2$ concentration.

After a suitable period in culture (normally not less than 1 hour and not exceeding 30 days), the cell containing capsules can be surgically implanted either directly, or by injection using a syringe into various areas.

At different times after the implantation of the encapsulated cells, the host can be treated with cyclophosphamide or ifosfamide either locally or systemically. Cells infected with the cytochrome P450 expressing virus will convert these prodrugs to the active metabolites which cause alkylation and cross-linkage of DNA. Also cells carrying and expressing the cytochrome P450 gene (such as encapsulated infected cells, or encapsulated packaging cells) will also catalyze this conversion. In one embodiment of this invention these encapsulated infected or packaging cells will be either slowly dividing cells, or cells that have been treated with mitomycin C, low doses of radiation, or other means to prevent cell replication, and thus to prevent the cells from being themselves affected by the cytotoxic effects of the prodrugs.

For safety considerations a replication defective retroviral vector, in which the genes encoding for viral proteins have been replaced by heterologous DNA sequences is used. According to still a further embodiment of the present invention said vector comprises a 5'LTR region of the structure U3-R-U5, one or more sequences selected from coding and non-coding sequences wherein at least one of the coding sequences codes for cytochrome P450 and a 3'LTR region comprising a completely or partially deleted U3 region. Said deleted U3 region is replaced by a polylinker sequence followed by the R and U5 region. In still a further embodiment said polylinker is used to introduce a heterologous promoter, a target cell specific promoter and/or regulatory element or an X-ray inducible promoter into the 31 LTR of the retroviral vector. After infection of a new host cell said 3' LTR with the heterologous promoter element becomes duplicated and translocated to the 5' LTR and subsequently, controls the expression of the retroviral vector genome including the cytochrome P450 gene inserted into the body of the retroviral vector.

Accordingly, said vector does not undergo self-inactivation but instead promoter exchange, giving rise to the name ProCon vector for Promoter Conversion vectors. The principles and advantages of the ProCon system are described in more detail in WO 96/07748. For a complete disclosure of the present invention the disclosure of WO 96/07748 is incorporated herein.

Since Promoter Conversion does not result in Self-Inactivation, the retroviral vector will be transcriptionally active in the target cell. Additionally both LTR's will consist to a large extent of heterologous promoter/enhancer sequences in the target cell. This will reduce the likelihood of the integrated vector in the target cell being subject to the same inactivation over long periods as has been described for conventional vectors (Xu, L., Yee, J. K. et al., *Virology*, 171:331–341 (1989)) and also will reduce the chance of recombination with endogenous retroviral sequences to generate potentially pathogenic replication competent virus, increasing the safety of the system.

According to the invention the 5'LTR of the retroviral vector construct is not modified, and expression of the viral vector in the packaging cells is driven by the normal retroviral U3 promoter. Normal retroviral polyadenylation is allowed, and no heterologous polyadenylation signals are included in the 3'LTR. This is important for the development of in vivo gene therapy strategies, since the normal physiological regulation of the virus, through the normal viral promoter, and possibly also involving the normal viral control of polyadenylation, will prevail over long periods in vivo whilst the packaging cells are producing recombinant virus.

The LTR regions used for a ProCon vector can be selected from at least one element of the group consisting of LTR's of Murine Leukemia Virus (MLV), Mouse Mammary Tumour Virus (MMTV), Murine Sarcoma Virus (MSV), Simian Immunodeficiency Virus (SIV), Human Immunodeficiency Virus (HIV), Human T-cell Leukemia Virus (HTLV), Feline Immunodeficiency Virus (FIV), Feline Leukemia Virus (FELV), Bovine Leukemia Virus (BLV) and Mason-Pfizer-Monkey virus (MPMV).

Alternatively, the retroviral vector is based on either a LXSN vector (Miller, A. D. and Rosman, G. J., Biotechniques, 7:980–990 (1989), PBAG (Price, J., Turner, D. et al., Proc. Natl. Acad. Sci. USA 84:156–160 (1987)) or a hybrid of both. The coding sequence of the therapeutic gene may be any cytochrome P450 gene but most preferably it is the rat cytochrome P450 form 2B1 defined by Fuji-Kuriyama, Y., Mizukami, Y., et al., Proc. Natl. Acad. Sci. USA 79:2793–2797 (1982)).

The promoters inserted into the 3'LTR can either be constitutive promoters such as the Cytomegalovirus (CMV) immediate early promoter/enhancer, inducible promoters such as promoters induced by glucocorticoid hormones (e.g., the MMTV promoter) or target cell specific promoters.

Such target cell specific regulatory elements and/or promoters are selected from one or more elements of any gene but preferably from promoters-such as carbonic anhydrase II, β-glucokinase regulatory elements and/or promoters, lymphocyte specific regulatory elements and/or promoters, Whey Acidic Protein (WAP) elements and/or promoters, Mouse Mammary Tumour Virus (MMTV) elements and/or promoters, β-lactoglobutin or casein specific regulatory elements and/or promoters, pancreas specific regulatory elements and/or promoters, immunoglobulin elements and/or promoters, MMTV lymphocytic specific regulatory elements and/or promoters, and/or MMTV specific regulatory elements and/or promoters conferring responsiveness to glucocorticoid hormones or directing expression to the mammary gland. Other promoters include for example the CD4, CD34, and IL2 promoters. Said regulatory elements and/or promoters regulate preferably the expression of said retroviral vector.

It appears that the region of the WAP promoter which is required for mediating the mammary gland specificity is a 320 bp XhoI/XbaI restriction fragment (−413 to −93) (Kolb, A. F., Günzburg, W. H., Albang, R., Brem, G., Erfle, V., and Salmons, B., Biochem. Biophys. Res. Commun., 217, 1045–1052 (1995)). In addition certain experiments indicate that a 0.6 Kb PstI MMTV promoter fragment (Salmons, B., Groner, B., Calberg Baca, C. M., and Ponta, H., Virology, 144:101–114 (1985)) may play a role in regulating the mammary gland specificity of expression displayed by MMTV (Kolb, A. F., Günzburg, W. H., Albang, R., Brem, G., Erfle, V., and Salmons, B., Biochem. Biophys. Res. Commun. 217, 1045–1052 (1995)).

According to standard protocols said retroviral vector is transfected into a packaging cell for the production of retroviral particles. Said packaging cells harbour at least one retroviral or recombinant retroviral construct coding for proteins required for said retroviral vector to be packaged. The packaging cells are either prepared from rodent, canine, feline or human cells or are chosen from one of the following cell lines: psi-2, psi-Crypt, psi-AM, GP+E-86, PA317 or GP+envAM-12, or of any of these supertransfected with recombinant constructs allowing expression of surface proteins from other enveloped viruses.

In the packaging cell line the expression of the retroviral vector is regulated by the normal unselective retroviral promoter contained in the U3 region of the 5'LTR. Accordingly, the packaging cell line and or the vector system is used to generate recombinant viruses that can be used to infect tumour or normal cells either in vitro or in vivo.

As soon as the recombinant virus infects the target cell promoter conversion occurs, and the P450 gene is expressed from a tissue specific or inducible promoter of choice inserted into the ProCon vector. Not only can virtually any tissue specific promoter be included in the system, providing for the selective targeting of a wide variety of different cell types, but additionally, following the conversion event, the structure and properties of the retroviral vector no longer resembles that of a virus. This, of course, has extremely important consequences from a safety point of view.

Recombinant retroviruses which have been purified or concentrated may be preserved by first adding a sufficient amount of a formulation buffer to the media containing the recombinant retrovirus, in order to form an aqueous suspension. The formulation buffer is an aqueous solution that contains a saccharide, a high molecular weight structural additive, and a buffering component in water. The aqueous solution may also contain one or more amino acids.

The recombinant retrovirus can also be preserved in a purified form. More specifically, prior to the addition of the formulation buffer, the crude recombinant retrovirus described above may be clarified by passing it through a filter, and then concentrated, such as by a cross flow concentrating system (Filtron Technology Corp., Nortborough, Mass.). Within one embodiment, DNase is added to the concentrate to digest exogenous DNA. The digest is then diafiltrated to remove excess media components and establish the recombinant retrovirus in a more desirable buffered solution. The diafiltrate is then passed over a Sephadex S-500 gel column and a purified recombinant retrovirus is eluted. A sufficient amount of formulation buffer is added to this eluate to reach a desired final concentration of the constituents and to minimally dilute the recombinant retrovirus, and the aqueous suspension is then stored, preferably at −70° C. or immediately dried. As noted above, the formulation buffer is an aqueous solution that contains a saccharide, a high molecular weight structural additive, and a buffering component in water. The aqueous solution may also contain one or more amino acids.

The crude recombinant retrovirus can also be purified by ion exchange column chromatography. In general, the crude recombinant retrovirus is clarified by passing it through a filter, and the filtrate loaded onto a column containing a highly sulfonated cellulose matrix. The recombinant retrovirus is eluted from the column in purified form by using a high salt buffer. The high salt buffer is then exchanged for a more desirable buffer by passing the eluate over a molecular exclusion column. A sufficient amount of formulation buffer is then added, as discussed above, to the purified recombinant retrovirus and the aqueous suspension is either dried immediately or stored, preferably at −70° C.

The aqueous suspension in crude or purified form can be dried by lyophilisation or evaporation at ambient temperature. Specifically, lyophilisation involves the steps of cooling the aqueous suspension below the glass transition temperature or below the eutectic point temperature of the aqueous suspension, and removing water from the cooled suspension by sublimation to form a lyophilized retrovirus. Once lyophilized, the recombinant retrovirus is stable and may be stored at −20° C. to 25° C., as discussed in more detail below.

Within the evaporative method, water is removed from the aqueous suspension at ambient temperature by evaporation. Water can also be removed through spray drying.

The aqueous solutions used for formulation, as previously described, are composed of a saccharide, high molecular weight structural additive, a buffering component, and water. The solution may also include one or more amino acids. The combination of these components act to preserve the activity of the recombinant retrovirus upon freezing and lyophilisation, or drying through evaporation.

The high molecular weight structural additive aids in preventing viral aggregation during freezing and provides structural support in the lyophilized or dried state. Within the context of the present invention, structural additives are considered to be of "high molecular weight (MW)" if they are greater than 5000 MW. A preferred high molecular weight structural additive is human serum albumin.

The amino acids, if present, function to further preserve viral infectivity upon cooling and thawing of the aqueous suspension. In addition, amino acids function to further preserve viral infectivity during sublimation of the cooled aqueous suspension and while in the lyophilized state.

The buffering component acts to buffer the solution by maintaining a relatively constant pH. A variety of buffers may be used, depending on the pH range desired, preferably between 7.0 and 7.8.

Aqueous solutions for the formulation of recombinant retroviruses are described in detail in WO-A2-96121014.

In addition, it is preferable that the aqueous solution contain a neutral salt which is used to adjust the final formulated recombinant retrovirus to an appropriate isosmotic salt concentration.

Lyophilized or dehydrated retroviruses may be reconstituted using a variety of substances, but are preferably reconstituted using water. In certain instances, dilute salt solutions which bring the final formulation to isotonicity may also be used. In addition, it may be advantageous to use aqueous solutions containing components known to enhance the activity of the reconstituted retrovirus. Such components include cytokines, such as IL-2, polycations, such as prolamine sulfate, or other components which enhance the transduction efficiency of the reconstituted retrovirus. Lyophilized or dehydrated recombinant retrovirus may be reconstituted with any convenient volume of water or the reconstituting agents that allow substantial, and preferably total, solubilization of the lyophilized or dehydrated sample.

Recombinant retroviral particles may be administered to a wide variety of locations including, for example, into sites such as an organ or to a site of a tumour. Within other embodiments, the recombinant retrovirus may be administered orally, intravenously, buccal/sublingual, intraperitoneally, or subcutaneously. The daily dosage depends upon the exact mode of administration, form in which administered, the indication toward which the administration is directed, the subject involved and the body weight of the subject involved, and further the preference and experience of the physician in charge.

The routes of administration described herein may be accomplished simply by direct administration using a needle, catheter or related device. In particular, within certain embodiments of the invention, one or more dosages may be administered directly.

The present invention also provides a pharmaceutical composition wherein the capsules encapsulating cytochrome P450 producing cells carrying the cytochrome P450 gene are mixed with a pharmaceutical acceptable carrier or diluent.

According to a further embodiment the capsules encapsulating cytochrome P450 producing cells and/or said pharmaceutical composition is used for the treatment of cancer or any other relevant disease or disorder. For an effective treatment of cancer according to the present invention a method comprising in addition to the implantation or injection of the capsules a systemic and/or local administration of the activatable prodrug is provided. This administration can be performed simultaneously together with the implantation or injection of the capsules. However, an administration of the prodrug with a time delay is possible as well. In a further embodiment of the present invention the prodrug is provided as a slow release preparation and/or encapsulated in a capsule comprising a porous membrane. This slow release preparation and also the encapsulated prodrug prolong the period, wherein prodrug is released at the site of application and thus, the cytochrome P450 catalyzes activation of toxic metabolites at said site of application.

According to the present invention the capsules are administered by injection or implantation into the target organ or close to said target organ. It proofed as advantageous according to still a further embodiment to inject the capsules directly into the artery which supplies the target organ to be treated, thus the capsules get flushed directly into the target organ. This is especially useful for the treatment of human pancreatic adenocarcinoma, since this tumour is not very suitable for resection. Additionally, this intra-arterial injection is also useful for any other tumour in organs of glandular tissue such as the breast, the kidney or the prostate gland.

In a further preferred embodiment ifosfamide or cyclophosphamide are used as prodrug. Furthermore, a therapeutic amount of 10 to 100 mg/m$^2$ body surface of said prodrug is applied to a patient in need thereof.

The detailed Examples which follow are intended to contribute to a better understanding of the present invention. However, it is not intended to give the impression that the invention is confined to the subject-matter of the Examples.

EXAMPLE 1

1. Isolation of the Cytochrom P450 2B1 (CYP2B1) Coding Region

1a. Isolation from a Plasmid

The cytochrome P450 2B1 coding region can be isolated from the plasmid, pSWI (Kedzie, K. M. et al., *J. Biol. Chem.* 266:22515–22521 (1991)), which was digested with XhoI/XbaI to yield two fragments. The 1.5 kb fragment containing the rat cytochrome P450 2BI cDNA, was excised and eluted using the Qiaquick DNA extraction protocol, ethanol precipitated and resuspended in water.

1b. Isolation from the Rat Hepatoma Cell Line HTC

For an alternative method to yield the rat cytochrome P450 2B1 gene, cells of the rat hepatoma cell line HTC were lysed with solution D (4 M guanidium thiocyanate, 25 mM sodium citrate pH 7, 0.5% N-laurylsarcosine sodium, 0.1 M 2-mercaptoethanol) and total RNA extracted by adding 1/15 volume of 3 M sodium acetate, in the same volume of water saturated phenol and 1/5 volume of chloroform/ isoamyalcolhol (49:1) were added and the whole mixture mixed vigorously. After 15 min on ice the extract was centrifuged 20 min at 4° C. at 10,000 g. The RNA in the aqueous phase was precipitated with one volume of isopropanol for 30 min at −20° C. and centrifuged at 10,000 g at 4° C. The pellet was washed in 70% ethanol and left at room temperature for 15 min. After 5 min centrifugation at 4° C. and 10,000 g the pellet was dried in a vacuum dryer and redissolved in 0.5% SDS solution. The extracted RNA was reverse transcribed using the protocol for cDNA synthesis (Pharmacia). The resulting cDNA was used as template for a PCR.

1c. Isolation from Rat Liver

Additionally, an alternative method to yield the mRNA from the rat cytochrome P450 form 2B1 is used. Therefore, a four week old female rat was sacrificed, the liver taken out and immediately frozen in liquid nitrogen. The frozen liver was put into sterilized filtered GTC-buffer (6 M guanidium isothiocyanate, 5 mM sodium citrate, 0.1 M 2-mercaptoethanol, 0.5% sodium N-laurylsarcosyl) and homogenized at room temperature. For RNA separation the liver extract was put onto a cushion of Caesium chloride (5.7 M Caesium chloride, 0.1 M EDTA) and centrifuged in a swing-out rotor at 20° C. and 32,000 rpm over night. After completely removing the supernatant the pelleted RNA was re-dissolved in ice cold 10 mM Tris pH 7.5 and precipitated overnight at −20° C. with $\frac{1}{15}$ volume 3 M sodium acetate and 2.5 volumes ethanol. The RNA was spinned down 40 min at 8000 rpm and 4° C. and the dried pellet resuspended in sterile water. The extracted RNA was reverse transcribed as described above.

2. Construction of a Cytochrom P450 2B1 (CYP2B1) Expressing Plasmid

2a. The plasmid pcDNA3 (Invitrogen) was digested with XhoI/XbaI and the resulting fragments dephosphorylated using calf intestine phosphatase. The DNA of the vector backbone was purified by separation on a 1% agarose gel, excision and preparation using the Qiaquick protocol (Qiagen). After ethanol precipitation the vector DNA was resuspended in water. Subsequently, 8.3 fMols of the pcDNA3 backbone and 24.8 fMols of the 1.5 kb fragment of pSW1 (as described under Example 1; item 1a) were mixed together and ligated for 1 day at 12° C. using T4-ligase (Boehringer). The ligase was inactivated at 65° C. for 10 min and the DNA butanol precipitated with a tenfold volume of butanol. The precipitated DNA was resuspended in water and electroporated into DH10B-bacteria (Gibco). Ampicillin resistant colonies were selected, DNA prepared and confirmed by restriction enzyme digestion as well as by sequencing. The final correct plasmid was designated pc3/2B 1.

2b. Alternatively, the plasmid pcDNA3 (Invitrogen) was digested with EcoRI/EcoRV and purified as described above. For the preparation of the CYP2B1 gene the cDNA as prepared according to Example 1 item 1b or 1c is used as PCR template. For this PCR, primer were designed that contained a EcoRI restriction site (underlined) in the left hand primer 5'-cgt gcg gaa ttc ggc gga ttc agc at-3' (SEQ ID NO.:1) and a EcoRV site (underlined) in the right hand primer 5'-ata acg gat atc acc tgg ctg cct ca-3' (SEQ ID NO:2). These primers had additional bases at the 5'-end for higher efficiency of the cutting enzyme. The 1588 bp-amplificate was digested with EcoRI and EcoRV. The resulting 1572 bp fragment, containing the gene for cytochrome P450 2B1, is subsequently ligated to the EcoRI/EcoRV digested and purified plasmid pcDNA3 (Invitrogen).

3. Stable Transfection of Cells to Express P450 2B1 Constitutively

Before the day of transfection, $3 \times 10^6$ feline kidney cells (Crandell, R. A., Fabricant:, C. G. & Nelson-Rees, W. A., In vitro 9:176–185 (1973)) were seeded into 100 mm dishes. On the day of transfection 4 μg of the plasmid pc3/2B1 was mixed with 100 μl serum free media. In parallel 15 μl Lipofectamine (Gibco/BRL) was mixed with 100 μl serum free media. The plasmid containing solution was added to the Lipofectamine-mix and incubated for 45 min. After 35 min the cells were washed once with 2 ml serum free media 800 μl of serum free media were added to the lipofection-mix and the resulting 1 ml was put onto the prepared cells. After 6 hours 1 ml DMEM (Glutamax) with 10% FCS was added. The next day the cells were trypsinised and diluted tenfold and seeded on a 100 mm dish. After 24 h the cells were given DMEM medium containing 400λg/ml G418. Resistant clones were isolated 14 days later and tested for presence and activity of the CYP2B1 expressing plasmid vector.

4. Functional CYP2B1 In Vitro Assays

Feline kidney cells carrying the CYP2B1 expressing plasmid vector were analyzed for expression of functional CYP2B1. This enzyme specifically dealkylates 7-pentoxy-resorufin to the fluorescent compound, resorufin. The expression of biologically active CYP2B1 in the transfectants was determined using a biochemical assay, which is specific for the cytochrome P450 isoforms 1A1 and 2B1 (Donato, M. T., Gomez-Lechon, M. J. & Castell, J. V., *Anal. Biochem*, 213:29–33 (1993)). Before the day of measurement different amounts of cells ($2.8 \times 10^6$, $5.5 \times 10^5$, $5.5 \times 10^4$) were seeded into a 3 cm dish. On the day of testing the cells were washed with phosphate buffered saline (PBS) and overlaid with 500 μl serum free medium containing 15 μm 7-pentoxy-resorufin (Sigma) and 10 μM dicumarol (Sigma). After a 30 min incubation period at 37° C., 375 μl of the supernatant was mixed with 125 μl of a 0.1 mM sodium acetate solution (pH 4.5) containing 75 Fishman units of β-glucuronidase/600 Roy units of arylsulfatase (Boehringer). The solution was incubated 2 h at 37° C. and the reaction stopped by adding 1 ml pure methanol. Precipitated proteins were pelleted at 7000 rpm and the amount of produced resorufin was measured with a fluorometer at 530 nm excitation and 590 nm emission. A standard curve was produced using different amounts of purified resorufin (Sigma).

Cells stably transfected with the CYP2B1 vector were shown to display CYP2B1 enzymatic activity proportional to the cell number analyzed. Typically one of the cell clones produces around 2 pmol/$10^5$ cells.

5. Functional CYP2B1 In Vivo Assays

Cells expressing CYP2B1 convert ifosfamide to metabolites (phosphoramide mustard and acrolein) which are cytotoxic for dividing cells. To test this suicide effects of ifosfamide on CYP2B1 expressing cells, 4×10 cells were seeded into a 3 cm dish. After overnight incubation in DMEM containing Glutamax (GIBCO) and 10% FCS, different concentrations of ifosfamide (0–5 mM) were added.

After five additional days the cells were trypsinised and an aliquot mixed with the same amount of 0.4% Giemsa in PBS, incubated for 1 min and the living cells counted. A drug induced suicide effect could be observed when the CYP2B1 expressing cells were grown in the presence of pharmacologically active concentrations of ifosfamide (0.25–2 mM). 0.25 mM is in the range of plasma drug concentrations (0.1–0.5 mM) observed after administration of the drug to patients (Wright, J. E. et al., *Analytical*

Biochemistry, 224:154–158 (1995)). Compared with cells not expressing CYP2B1 which were not affected by the above mentioned concentrations of the prodrug, in cells expressing CYP2B1 a tenfold higher sensitivity to ifosfamide or cyclophosphamide was shown.

6. Bystander Effect of CYP2B1 Expressing Cells

The ability of genetically modified cells that activate a prodrug to also affect surrounding non-modified cells has been termed a bystander effect.

To test the bystander effect, $3 \times 10^5$ of β-galactosidase expressing feline kidney cells were added to $3 \times 10^5$ CYP2B1 expressing cells on the first day. After overnight incubation in DMEM containing Glutamax (GIBCO) and 10% FCS, different concentrations of ifosfamide (0–5 mM) were added. On the seventh day the cells were washed twice with PBS and fixed with 2% paraformaldehyde in PBS for 20 min. The cells were rinsed twice with PBS, covered with 1 ml staining solution (0.4 mM $K_3Fe\,(CN)_6$, 0.8 mM $K_4Fe\,(CN)_6$, 0.004 mM $MgCl_2$ in PBS) containing 25 µl of 40 mg/ml X-Gal (5-bromo-4-chloro-3indolyl β-D-galactopyranoside) in dimethylformamide and were incubated overnight at 37° C.

Co-cultivation of CYP2B1 expressing and non-expressing cells (e.g. Feline kidney cells as well as pancreatic tumour derived Rin5 cells) demonstrated that non-expressing cells could also be killed by the toxic metabolites of ifosfamide produced by the CYP2B1 expressing cells. The titration studies revealed that as little as 0.25 mM ifosfamide causes specific toxic effects on these cells and 1–2 mM results in the death of all cells.

To proof that this bystander effect is not dependent on direct cell-to-cell contact, as is the case for the HSV-tk mediated effect (Elshami, A. A. et al., *Gene Therapy* 3:85–92 (1996)) but is mediated by a freely diffusable metabolite, cells expressing CYP2B1 and non-expressing reporter cells were separated by a filter with 0.45 µm pores.

To additionally simulate a situation during treatment of a pancreatic tumour, a human pancreatic tumour derived cell line, PANCl (Löhr, M. et al., *Br. J. Cancer*, 69:144–151 (1994)) was used. For the filter assay $3 \times 10^5$ CYP2B1 expressing and $3 \times 10^5$ reporter (PANC1) cells were seeded on the first day, but separated by a membrane with 0.45 µm pores. After overnight incubation in DMEM containing Glutamax (GIBCO) and 10% FCS, different concentrations of ifosfamide (0–5 mM) were added. On the seventh day the reporter cells were stained with trypan blue and the living cells counted. The combination of non-CYP2B1 expressing cells and PANC1 cells showed no significant change in cell number or viability when treated with pharmacologically active ifosfamide concentrations. In contrast, the PANC1 cells that were seeded together with CYP2B1 expressing cells showed a significant decrease in the survival of PANC1 (and CYP2B1 expressing) cells already at a concentration of 0.25 mM ifosfamide. This bystander effect became more pronounced with increasing concentrations of ifosfamide. Only at a concentration of 5 mM ifosfamide a CYP2B1 independent nonspecific cytotoxicity of ifosfamide was observed.

7. Encapsulation of CYP2B1 Expressing Cells and Characterisation

7a. Encapsulation

The CYP2B1 expressing cells were encapsulated in cellulose sulfate for immobilization in the tumour and for protection from the immune system. Capsules were produced as follows: $1 \times 10^7$ CYP2B1 transfected cells were suspended in 1 ml PBS (pH 7) containing 2–5% cellulose sulfate and 5% FCS (Gibco/BRL). The suspension was allowed to drop freely from an adjustable dispersion system by regulating the flow into a precipitation bath containing 3% polydiallyldimethyl ammonium in PBS. Capsule formation occurred within milliseconds followed by further constitution of an inner, more porous, layer for mechanical support. Capsules were washed twice with normal medium (RPMI) and then either taken into tissue culture or if empty stored in PBS at 40° C. until further processing. Thereby produced cellulose sulfate capsules have a diameter from 0.01 to 5 mm, preferably 200–500 µm which pass comfortably through a 21 G needle (inner diameter 0.6 mm). Typically, a 200 µm capsule contains up to $10^4$ cells and single capsules could be shown to yield 0.15 pmol CYP2B1 by the resorufin assay. This compares favorably with the levels detected from these cells in normal culture conditions (i.e. about 2 pmol/$10^5$ cells). Furthermore, the enzyme activity could be detected up to 4 weeks after encapsulation of transfected cells, confirming that the cells remain viable in the capsules.

7b. Integrity of the Capsules

The integrity of empty and cell filled capsules after flushing through a 19G needle with a 1 ml standard syringe was confirmed by phase contrast and electron microscopy. After repeated passing through the needle, the capsules were also placed in tissue culture for several weeks. No outgrowth of cells from these capsules was observed during the 6 week observation period, indicating that the capsules were still intact.

7c. Vitality of the Encapsulated Cells

The vitality of the encapsulated cells was measured with the two-color Life&Dead Viability/Cytotoxicity Kit (MobiTec, Braunschweig, Germany) which show a green fluorescence (calcein) for living cells and a red fluorescence (ethidiurn bromide) for dead cells. Samples were processed according to the manufacturer's recommendations. Encapsulated cells were analyzed with a confocal laser microscope (Zeiss).

Additionally, different storage conditions (4° C. and 37° C.) were analyzed. Cells at the outer edge of the capsules tended to survive longer than those in the center of the capsules. At 4° C. approximately 90% of the cells were alive 4 weeks after encapsulation, and at 37° C. around 70% of the cells were alive 4 weeks after encapsulation. As shown above the viability of high percentage encapsulated cells expressing P450 up to 4 weeks can be guaranteed both at 37° C. or at 40° C. To avoid a cytotoxic effect of the synthesized cytocbrome P450 to the encapsulated cells during ifosfamide treatment, cell division was inhibited. Therefore, freshly prepared capsules containing P450 expressing cells were incubated for at least 2 hours with mitomycin C (1 µg/ml). The mitomycin C treatment did not affect the P450 production or activity over a 30 day period.

8. In Vivo Toxicity of Capsules

To assess possible effects of the capsule material in mice, empty capsules were injected orthotopically into the pancreas of both CD-1 nu/nu nude and immunocompetent Balb/c mice (Charles River, Germany). As demonstrated by the injection of empty capsules in the unaffected pancreas of both nude and immunocompetent mice, minimal tissue reaction or pancreatitis could be observed seven days after injection. The only observed tissue reactions in both situations were a few granulocytes and lymphocytes surrounding the capsule. No pancreatitis could be observed on the morphological level nor did the animals express signs of illness. In case of the pancreas, this is an important issue since the organ is very sensitive to manipulation and ischemia. Injection of adenovirus for gene therapy into the pancreatic duct, for instance, caused pancreatitis. Thus, the local application of such capsules even in very sensitive body regions seems feasible.

9. Treatment of Spontaneous Tumours of Balb/c or GR Mice

The capsules obtained are implanted by "key hole" surgery near or in either transplanted or spontaneous tumours of BALB/c or GR mice. About six capsules of about 1 mm diameter are inserted at each operation site. The site of surgery is closed by one suture. The mice are then treated with cyclophosphamide or ifosfamide locally, by direct intratumoural injection of 100 µl of 20 mg/ml or systemic concentrations of 130 mg CPA/kg body weight i.p. and 40–60 mg IFO/kg body weight i.p. for up to a maximum of 10 weeks. During this period tumour size and macroscopic appearance is monitored daily. The mice are then sacrificed, the tissue containing the inserted capsules and tumour removed, and histological sections for light and electron microscopy prepared. These sections clearly show good engraftment of the capsules, vascularisation, and no evidence of the presence of lymphocytes indicative of a cellular immune response. These sections also show no sign of cell death or necrosis within the capsule. In contrast the tumour showed necrosis and macroscopically there was a clear reduction in size over the test period.

10. Treatment of Pre-Established Tumours

To determine the effects of local CYP2B1 expression on ifosfamide treatment of preformed tumours, induced by subcutaneous injection of PaCa-44 human pancreatic tumour cells into nude mice. Said human pancreatic carcinoma cell line PaCa-44 derived from a typical adenocarcinoma of moderate to poor differentiation (G2-3) and has been extensively characterized. The cell line carries mutations in codon 12 of the =ras oncogene and mutations in exon 5/6 of the p53 tumour suppresser gene while RB1 is wild type. PaCa-44 cells were grown in RPMI with, 10% FCS supplemented with penicillin and streptomycin (Gibco/BRL).

For establishing a tumour in the nude mouse $1 \times 10^6$ cells were injected subcutaneously in the flanks of nude mice (CD-1 nu/nu; Charles River, Germany) in RPMI without supplements. Tumours were allowed to grow for 7 to 10 days. When the resultant tumours had reached a size of 1 cm$^3$, either $1 \times 10^6$ CYP2B1 expressing cells or 20–40 capsules carrying CYP2B1 expressing cells were injected into the tumours and/or the animals treated systemically with ifosfamide.

To start the experiment several groups were defined: (1) controls with no treatment and no injection; controls with injection of transfected fibroblasts (2) with and (3) without encapsulation but without ifosfamide treatment; and three treatment groups encompassing (4) no injection of cells, (5) injection of naked cells and (6) injection of encapsulated cells (Table 1). $1 \times 10^6$ cells were suspended in 100 µl RPMI, filled into a 1 ml standard syringe (B. Braun, Melsungen, Germany) and injected through a 29G needle (Microlance 3, Becton Dickinson, Fraga, Spain). Capsules were delivered through a 21G needle (Microlance 3, inner diameter 0.6 mm) into the tumour. Approximately 20–40 capsules were delivered per injection. Animals were treated intraperitoneally every third day for 2 weeks with 100 mg/kg body weight ifosfamide (Holoxan; Asta Medica, Frankfurt/M, Germany). At the same time, sodium 2-mercaptoethanesulfonate (MESNA; Asta Medica) was administered i.v. at the same dosage (100 mg/kg body weight) via the tail vein.

As expected, due to endogenous conversion of ifosfamide by the liver, tumour growth was inhibited in mice that received ifosfamide treatment, regardless of the presence or absence of CYP2B1 expressing cells, compared to all of the non-treated groups. However, tumour reduction was most pronounced in mice that received encapsulated CYP2B1 expressing cells by injection into the tumour and subsequent treatment with ifosfamide (Table 1). Indeed, a complete disappearance of macroscopic and microscopic tumour growth was observed in 4 cases. The therapeutic effect was defined analogously to the terms complete response (CR), i.e. total disappearance of the tumour and partial response (PR), i.e. more than 50% reduction of tumour mass.

Microscopic examination of the tumours after treatment, however, did not always demonstrate the presence of the capsules. Since the capsules are most likely located in the center of necrotic areas within the tumour, this is possibly a result of their loss during cutting and processing when they could be washed out with the almost liquid necrotic tumour tissue. This is supported by the observation that such injected capsules are easily found after injection into normal organs such as the pancreas or in the cleared mammary fat pad.

TABLE 1

Experimental Groups of Nude Mice and Results after Treatment with Ifosfamide

| Group | CYP2B1 cells | Treatment | Number of animals | CR | PR$ & CR | Necrosis* % Mean |
|---|---|---|---|---|---|---|
| 1 | No | None | 11 | 0 | 0 | 10% |
| 2 | yes/naked | None | 6 | 0 | 0 | 10% |
| 3 | yes/encapsulated | None | 3 | 0 | 0 | 23% |
| 4 | no | ifosfamide | 10 | 0 | 3 | 22% |
| 5 | yes/naked | ifosfamide | 11 | 0 | 3 | 16% |
| 6 | yes/encapsulated | ifosfamide | 22 | 4 | 12 | 45% $P < 0.0001$# |

*Complete Responders (CR) with either 100% necrosis or no tumor visible were scored 100%.
$Partial Responders (PR) were scored as mice with tumors of a diameter of 1.5 cm or less at completion of treatment regime. Untreated animals scored tumor sizes of, on average, 2.5–3.0 cm at completion.
In a paired t-test comparing to group 4, this was highly significant.

11. BrdU Assay on Actively Dividing Cells

To analyze whether beside the clear reduction of tumour mass still actively dividing tumour cell were present a BrdU assay was performed. Therefore, BrdU was administered at 100 mg/kg body weight i.p. 6 hours prior to harvesting the tumour tissue from anaesthetized animals. The tumours were measured, cut in half and snap frozen immediately after removal from the animal 4 µm sections were cut. Samples were processed according to the manufacturer's instruction (In situ Cell Proliferation Kit, AP; Boehringer Mannheim).

It could be shown that along with marked necrosis of the tumours, the BrdU labeling index was also dramatically reduced in the group treated with encapsulated CYP2B1 expressing cells, indicating that any remaining tumour cells were not actively dividing. In one particular animal, although a nodule was macroscopically visible, it displayed a complete cystic degeneration indicating eradication of the tumour. Even though the ifosfamide dosage was identical in all of the treated mice, animals treated with encapsulated cells also appeared healthier compared to those injected directly with CYP2B1 expressing cells which at best showed only a partial response (Table 1).

12. Safety Aspects

In another study, the CYP2B1 gene was transfected directly into breast cancer cells. Treatment with either cyclophosphamide and ifosfamide resulted in cell killing and after implantation in nude mice, tumour regression. This approach demonstrated the power of local delivery of the enzyme converting the cytotoxic drug locally into its active form. However, the genetic modification of tumour cells, whilst an elegant method to show proof of principle, cannot easily be applied in the clinic. Delivery of CYP2B1 transfected cells, if encapsulated according to the present invention, is a feasible clinical approach involving no direct gene therapeutic intervention in the patient. To demonstrate the safety of the encapsulated cells PCR with primers specific for the expression construct pc3/2B1 were performed from all organs including the brain and blood of injected tumour-bearing animals.

No PCR product was found in tumour material from around the capsule implantation area of mice that were not treated with ifosfamide nor in any other organ tested.

EXAMPLE 2

1. Construction of Cytochrome P450 2B1 (CYP2B1) Expressing Retroviral Vector

1a. Retroviral Vector Derived from pLX125

This Examples describes the construction of a retroviral expression vector for intratumoural infection which contains the gene for rat cytochrome P450 2B1. The new expression vector pLX2B1, was constructed by ligation of fragments obtained from plasmid pLX125, disclosed in PCT/EP96/04447, and pSW1, as described in Example 1, item 1a. Therefore, the plasmid pLX125 was linearized with HpaI and the resulting blunt ends dephosphorylated using calf intestine phosphatase. The DNA was purified by separation on a 1% agarose gel, excision and preparation using the Qiaquick protocol (Qiagen). After ethanol precipitation the DNA was resuspended in water. In parallel the cloning vector pSW1 was digested with SmaI/HincII to yield two blunt ended fragments. The digestion mixture was separated on a 1% agarose gel. The shortest fragment (1.5 kb) containing the rat cytochrome P450 2B1 cDNA was excised and eluted using the Qiaquick DNA extraction protocol, ethanol precipitated and resuspended in water. 7.6 fMols of pLX125 and 24 fMols of the SmaI/HindIII 1.5 kb fragment of pSW1 were mixed together and ligated for 3 days at 12° C. using T4-ligase (Boehringer). The ligase was inactivated at 65° C. for 10 min and the DNA butanol precipitated with a tenfold volume of butanol. The precipitated DNA was resuspended in water and electroporated into DH10B-bacteria (Gibco). Ampicillin resistant colonies were selected, DNA prepared and test digested with SspBI/SalI, BamHI/SspBI, PvuI and BamHI. The final correct plasmid was designated pLX2B1.

Alternatively, a retroviral expression vector—based on pLX125—which contain the gene encoding rat-cytochrome P450-2B1 can be prepared also as described in the following: Firstly, the plasmid pLX125 is partially digested with the restriction enzyme XhoI to yield a vector which is linearized at position 3547. This linear plasmid was further digested with the restriction enzyme SspBI to remove a short fragment within the polylinker of pLX125. In a preparative gel the correctly cut vector fragment appeared as the largest band. Using the Qiaex protocol, (Qiagen) the DNA in this band was eluted and purified from the gel.

Additionally, the 1562 bp-fragment from the XhoI/SspBI digest of the PCR product obtained using specific primers. These primers were designed to have a SspBI restriction site (underlined) in the left hand primer 5'-aag cct gta cac tgg aga gca tgc ac-3' (SEQ ID NO:3) and a XhoI site (underlined) in the right hand primer; 5'-cga tta ctc gag acc tgg ctg cct α-3' (SEQ ID NO:4). The PCR amplification product is digested with the restriction enzymes SspBI/XhoI resulting in a 1545 bp fragment, containing the gene for cytochrome P450, is ligated into the XhoI/SspBI digested retroviral vector pLX125.

1b. Retroviral Vector Derived from pWAP.6

While retroviral vector derived from pLX125 carry a MMTV-U3 region in its 3'LTR, which after infection controls expression of the viral genome, the retroviral vector derived from pWAP.6 controls after infection a heterologous DNA from a target specific WAP promoter (ct. PCT/EP96/03922). For this, the plasmid pWAP.6 is digested with BamHI and purified. The CYP2B1 gene is isolated from the cDNA as described under Example 1, item 1 performing a PCR with primers incorporating a BamHI site (underlined) 5'-aag ccg gat ccc tgg aga gca tgc α-3' (SEQ ID NO:5) and 5'-cga tta gga tcc ctg cct α-3' (SEQ ID NO:6). The 1562 bp PCR fragment, containing the gene for cytochrome P450, is digested with BamHI and ligated to the prepared pWAP.6 vector.

2. Construction of a Retroviral Packaging Cell Line Expressing Cytochrome P450 and Releasing Cytochrome P450 Transducing Retroviral Particles.

For the construction of a retroviral packaging cell line releasing a cytochrome P450 transducing retroviral vector an established packaging cell line PA317 (Miller & Buttimore, *Mol. Cell Biol.*, 6:2895–2902) is transfected—using the same protocol as described under Example 1, item 3—with the retroviral vector of Example 2, item I. After a selection period of 14 days cell populations were isolated and analyzed for expression of cytochrome P450.

3. Infection of Target Cells with Retroviral Vectors Transducing Cytochrome P450

Supernatant from positively tested cell populations of Example 2, item 2 is subsequently used to infect target cells. Thus, 1 ml of virus containing supernatant from $5\times10^6$ cells was filtered through a 0.45 µm filter and added to $1\times10^6$ target CK cells in the presence of 8 µg/ml Polybrene. After 4 hours ml of Dulbecco's Modified Eagles Medium with 10% Fetal Calf Serum was added. Subsequently, cells were trypsinised the next day, diluted and 24 hours later put in selection medium containing additionally 400 µg/ml G418. After 2 weeks G418 resistant colonies were isolated and tested for cytochrome P450 2B1 activity. $2\times10^4$ cells were plated onto a 3 cm dish and exposed to concentration of ifosfamide varying between 0 and 5 mM. A higher sensitivity of the cytochrome P450 2B1 retrovirus infected cells was observed compared to control, non-infected cells.

4. Encapsulation of Retroviral Vector Producing Packaging Cells or Cells Infected with a Retroviral Vector.

Retroviral packaging cells, as described in Example 2, item 2, or cells infected by a retroviral vector, as described in Example 2, item 3, are packaged according the method as described in Example 1, item 7.

EXAMPLE 3

1. Treatment of Human Pancreatic Cancer

For the therapeutic treatment of a tumour in a human being the pancreatic cancer was selected as a model system. The prognosis of pancreatic adenocarcinoma is poor and current treatment ineffective. Administration of ifosfamide to tumour bearing mice that received the encapsulated cells results, as demonstrated in Example 1 item 10, in partial or even complete tumour ablation. These results clearly show that in situ chemotherapy with genetically modified cells encapsulated in an immunoprotected environment is useful for application also in man.

To adjust the treatment strategy to a human as patient, the number of CYP2B1 expressing cells encapsulated in an immunoprotected environment to inject to the tumour must be increased by administering 200 to 500 capsules each carrying around $10^4$ cells expressing around 0.15 pmol/capsule. The preferred route of application of the encapsulated cells is angiografically into the artery, which directly leads to the pancreas. Capsules will thereby spread out in the organ without mechanically injuring the organ e.g. by an injection needle. However, the mode of administrating the capsules can be optimized by those skilled in the art in a known manner.

As demonstrated by the Example 1 the best mode of locally treating a tumour in an animal according to the invention was seen, when using an encapsulated population of cells expressing around 2 pMol CYP2B1 per $10^5$ cells and systematically administering an activatable chemotherapeutic, such as ifosfamide at a final concentration of 100 mg per kg body weight. However, this is not comparable to the effective amount necessary in humans. Calculating a therapeutic dose for a human mg/kg body weight is not normally used, but a dose calculation based on mg/m$^2$ body surface is used. According to the present invention for the local treatment of humans a therapeutic dose in the range of 10 mg to 1000 mg ifosfamide per m$^2$ body surface was applied.

The invention may be worked according to numerous equivalent or similar procedures all being well known in the art and all of such equivalent or similar procedures to obtain and effect the steps of the present invention, will be appreciated as such by any person of average skill in the art, and should be considered part of and comprised by the present invention and application and the invention is therefore only to be limited by the full scope of the appended claims.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A capsule comprising a porous membrane formed by a polyelectrolyte complex which encapsulates cells which express cytochrome P450 as a cell membrane-bound protein, wherein the porous membrane of the capsule is permeable to prodrug molecules and the cells are retained within the capsule.

2. The capsule according to claim 1, wherein the capsule material comprises a complex formed from cellulose sulphate and polydimethyldiallylammonium.

3. The capsule according to claim 1, wherein said capsule comprises cellulose sulphate.

4. The capsule according to claim 1, wherein said capsule comprises polydimethyldiallylammonium.

5. The capsule according to claim 1, wherein the capsule comprises a cellulose based material.

6. The capsule according to claim 1, wherein the polyelectrolyte complex comprises a sulphate group.

7. A pharmaceutical composition comprising the capsule according to claim 1.

8. The capsule according to claim 1 wherein the cytochrome P450 is cytochrome 2B1.

9. A method for ablation of tumour cells, comprising administering locally into said minor cells or close to the site of said tumor cells, prodrug molecules and a capsule wherein the capsule comprises a porous membrane formed by a polyelectrolyte complex which encapsulates cells which express cytochrome P450 as a cell membrane-bound protein, wherein the porous membrane of the capsule is permeable to the prodrug molecules, the cells are retained within the capsule, and the prodrug molecules are converted into active drug molecules by cytochrome P450 and thereby ablate the rumor cells.

10. A method of treating a tumor comprising administering to a subject in need thereof a therapeutically effective amount of a capsule and, either simultaneously or with a time span, a prodrug which is activated by cytochrome P450, wherein the capsule comprises a porous membrane formed by a polyelectrolyte complex which encapsulates cells which express cytochrome P450 as a cell membrane-bound protein, the porous membrane of the capsule is permeable to the prodrug cells are retained within the capsule and the capsule is introduced into the tumor or next to the tumor.

11. The method according to claim 10, wherein the capsule is administered by a route of administration selected from the group consisting of: injection into the target cells, implantation into the target cells and combinations thereof, wherein the prodrug is administered systemically, locally or systemically and locally.

12. The method according to claim 10, wherein the target cells are cells of breast tumours and/or pancreatic tumours.

13. The method according to claim 10, wherein the prodrug is cyclophosphamide and/or ifosfamide.

14. A pharmaceutical kit comprising capsules according to claim 1 and a prodrug which is activated by cytochrome P450.

15. The pharmaceutical kit according to claim 14, wherein the capsules and the prodrug are formulated so that the capsules, which are administered into a target or next to the target, and the prodrug can be adminstered by different routes of administration.

16. The pharmaceutical kit according to claim 15, comprising the capsule in the form suitable for an injection or implantation into the target organs or next to the target organ, and the prodrug in the form suitable for systemic or local administration.

17. The pharmaceutical kit according to claim 14 comprising the capsules in the form suitable for the implantation into and/or next to breast cancer tissue or pancreatic cancer tissue.

18. The pharmaceutical kit according to claim 14 comprising cyclophosphamide and/or ifosfamide as the prodrug.

19. The method according to claim 9 wherein the prodrug is selected from the group consisting of cyclophosphamide and ifosfamide.

20. The capsule according to claim 8 wherein the cytochrome P450 2B1 is derived from rat liver.

21. The capsule according to claim 1 wherein the cytochrome P450 is encoded by a mammalian expression vector.

* * * * *

UNITED STATES PATENT AND TRADEMARK OFFICE
CERTIFICATE OF CORRECTION

PATENT NO. : 6,893,634 B1
DATED : May 17, 2005
INVENTOR(S) : Günzburg et al.

It is certified that error appears in the above-identified patent and that said Letters Patent is hereby corrected as shown below:

<u>Title page,</u>
Item [75], Inventors, delete "Peter Müller" and insert -- Petra Müller --.

Signed and Sealed this

Seventh Day of March, 2006

JON W. DUDAS
*Director of the United States Patent and Trademark Office*